(12) United States Patent  (10) Patent No.: US 8,063,932 B2
Boyer et al.  (45) Date of Patent: Nov. 22, 2011

(54) CAMERA FOR MEDICAL, PARTICULARLY DENTAL USE

(75) Inventors: Philippe Boyer, Marseilles (FR); Alain Mazuir, Saint Maximin (FR)

(73) Assignee: Sopro, La Ciotat (FR)

( * ) Notice: Subject to any disclaimer, the term of this patent is extended or adjusted under 35 U.S.C. 154(b) by 1466 days.

(21) Appl. No.: 10/588,189

(22) PCT Filed: Feb. 25, 2005

(86) PCT No.: PCT/FR2005/000456
§ 371 (c)(1),
(2), (4) Date: Aug. 2, 2006

(87) PCT Pub. No.: WO2005/089631
PCT Pub. Date: Sep. 29, 2005

(65) Prior Publication Data
US 2007/0126865 A1   Jun. 7, 2007

(30) Foreign Application Priority Data
Mar. 1, 2004 (FR) ...................................... 04 02090

(51) Int. Cl.
*H04N 7/18* (2006.01)
(52) U.S. Cl. ............................... 348/66; 348/74; 433/29
(58) Field of Classification Search .................. None
See application file for complete search history.

(56) References Cited

U.S. PATENT DOCUMENTS

| 5,771,067 A * | 6/1998 | Williams et al. ................. 348/66 |
| 5,861,002 A * | 1/1999 | Desai .............................. 606/210 |
| 6,249,348 B1 * | 6/2001 | Jung et al. ...................... 356/419 |
| 6,867,380 B2 * | 3/2005 | Miki et al. ..................... 200/5 R |
| 7,139,016 B2 * | 11/2006 | Squilla et al. ................... 348/66 |
| 2002/0049464 A1 * | 4/2002 | Donofrio et al. .............. 606/169 |
| 2004/0217945 A1 * | 11/2004 | Miyamoto et al. ............. 345/173 |

* cited by examiner

*Primary Examiner* — Christopher S Kelley
*Assistant Examiner* — Christopher Findley
(74) *Attorney, Agent, or Firm* — Young & Thompson

(57) ABSTRACT

The medical, particularly dental imaging camera including an elongated housing (2) that can be held by a single hand of a user and provided, at its front end, with an imaging element, this housing (2) including a sensitive control element capable of freezing, on a display (5), an image selected by the user, this control element having a detection area (9) situated on the housing (2) that is delimited by a surface discontinuity such as a recess or a relief (11). The housing (2) encloses a sensor element associated with an electronic driving circuit and an electrostatic foam element whose one end is applied against the sensor element and whose opposite end is applied against an area of the inner face of the housing (2) located to the right of the detection area (9).

12 Claims, 1 Drawing Sheet

CAMERA FOR MEDICAL, PARTICULARLY DENTAL USE

BACKGROUND OF THE INVENTION

1. Field of the Invention

The present invention relates to a camera for medical, and particularly dental, use.

2. Description of the Related Art

In the medical domain, and more particularly in the dental domain, micro-cameras are known, whose lens is disposed at the end of a hand piece and which comprise on the body thereof a control knob making it possible to trigger off shot-taking or to capture a specific image.

Such micro-cameras, particularly when they are used in applications where it is necessary to "freeze" an image, are controlled by a specific pedal actuated by the user's foot. In effect, it has been observed that, particularly in this type of applications, the simple actuation of a control knob fast with the camera, however gentle its release, led to generating a movement of the camera having for effect to blur the image which it was desired to "freeze". Now, this type of pedal-control is used for numerous instruments, particularly in dental surgeries, with the result that it may be awkward for the practitioner to multiply such controls.

Furthermore, different types of release controls which do not require any physical displacement of the user's fingers, are known, such as for example the controls of sensitive type which are constituted in particular by capacitive or inductive sensors which react to the electric field produced by a user's finger.

One of the difficulties encountered in the use of such controls on dental cameras for ensuring "freezing" of an image, is a result of the fact that, contrary to the conventional control knobs which allow a tactile localization, the sensitive controls can themselves only be localized by the practitioner visually, which is not acceptable in the present case insofar as his visual concentration must imperatively be directed on the operative field.

This is why Patent Application FR 02 15014 proposed to provide on the outer face of the body of the camera a zone of surface discontinuity, forming a crest or a hollow, which is disposed plumb with the sensitive sensor, and which allows the user to ensure positioning of his finger with respect to the zone of detection slightly upstream thereof, it being understood that any additional movement of this finger will provoke its detection and consequently the triggering of the appropriate control.

Control systems of sensitive type are usually composed of a sensor (generally a metal pellet) and of electronic means disposed on a support circuit. Now, it has proved that, for various reasons, due in particular to the space requirement, to the global design of the camera, to the aesthetics of the body thereof, or to the presence of various components on the support circuit, it is not possible, in certain configurations, to dispose the sensor and the electronic circuit associated therewith in contact with the inner face of the body of the camera. Now, it is known that, when it is desired that the sensor detects a user's finger precisely and repetitively, it cannot be envisaged to separate the electronic circuit from the sensor in order to position the latter against the inner wall of the body in the immediate proximity of the zone of detection. In effect, it has been observed that the cord link which is in that case established between these two elements has for consequence to destroy the precision and correct repetitivity of the position of detection, insofar as the linking cords become an integral part of the sensor, their position and their length influencing the detection.

SUMMARY OF THE INVENTION

It is an object of the present invention to propose a means for disposing the sensor and its support circuit apart from the zone of detection while conserving the qualities of precision and repetitivity which would have existed if this sensor were disposed in the immediate proximity thereof.

The present invention thus has for its object a camera for medical, particularly dental, use, comprising an elongated casing adapted to be held in a user's hand and provided at its anterior end with image-taking means, this casing comprising control means of sensitive type adapted to "freeze" on display means an image chosen by the user, these control means comprising a zone of detection located on the casing which is defined by a surface discontinuity such as a hollow or a crest, characterized in that the casing contains a sensor element associated with an electronic piloting circuit and an electrostatic foam element of which one end is applied against the sensor element and its opposite end is applied against a zone of the inner face of the casing disposed plumb with the zone of detection.

The electrostatic foam element, when it is in position between the inner face of the casing and the sensor element, will preferably be in a slightly compressed state.

Furthermore, in a variant embodiment of the invention allowing positioning of the support circuit of the sensor element in the casing to be facilitated, that part of the foam element which is in contact with the sensor element will have a larger surface than that of this sensor and in that case the resistivity of this part will be given a value which will be greater than the resistivity of the central part of the foam element. Furthermore, the resistivity of that part of the foam element in contact with the inner face of the casing may be less than the resistivity of the central part of the foam element. The resistivity of the foam element will preferably be less than 5 MΩ.cm.

BRIEF DESCRIPTION OF THE DRAWING FIGURES

A form of embodiment of the present invention will be described hereinafter by way of non-limiting example, with reference to the accompanying drawings, in which.

DETAILED DESCRIPTION OF THE INVENTION

Figure 1:
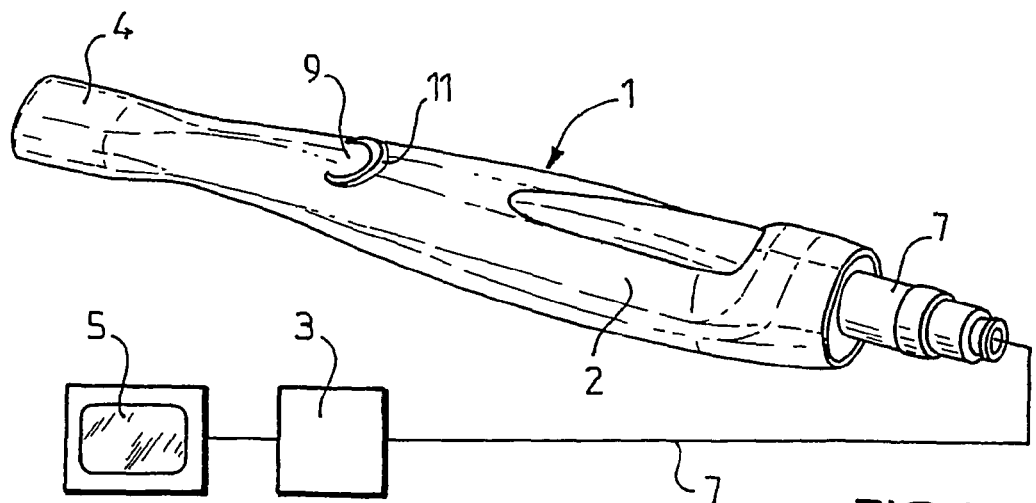
FIG. 1 is a view in perspective of a camera according to the invention.
Figure 2:
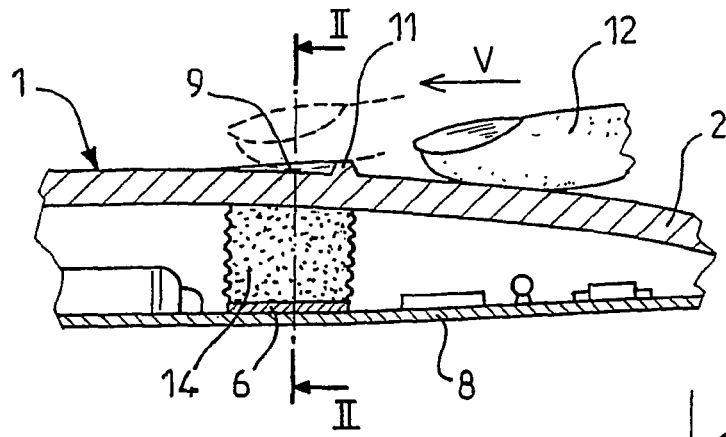
FIG. 2 is a partial view in vertical and longitudinal section of the camera shown in FIG. 1.
Figure 3:
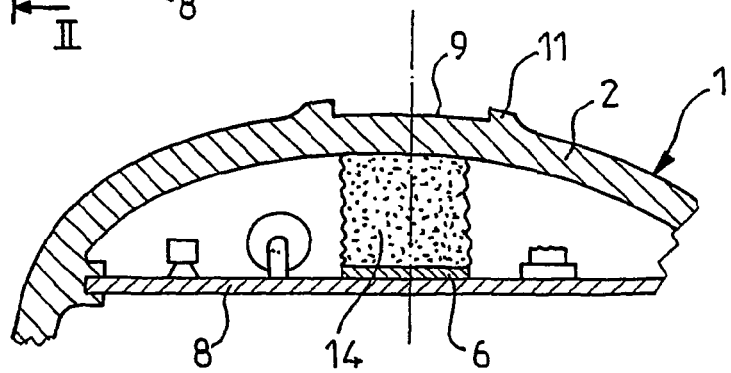
FIG. 3 is a view in transverse section of the camera shown in FIG. 1, along line II-II of FIG. 2.

FIGS. 1 to 3 show a dental camera 1 which is constituted by an elongated body 2, of substantially ellipsoidal cross section, comprising at its anterior end 4 a shot-taking lens and at its other end a cord 7 by which it is linked with electronic means 3 for supply and for managing the images which are displayed on a monitor 5.

According to the invention, this camera 1 comprises a control device allowing the user to "freeze" an image, i.e. to immobilize it on the monitor 5. This control device comprises a sensitive sensor associated with an electronic circuit, and a zone of surface discontinuity made on the casing 2.

The zone of surface discontinuity is formed by a boss 11 in the form of a C whose opening is oriented towards the anterior end 4 of the camera and which projects slightly with respect to the upper face of the body 2. The boss 11 is disposed upstream of a zone 9 (called detection zone 9) with respect to the movement of natural displacement of a finger 12 of the user when he holds the camera 1, namely the direction represented by arrow V in FIG. 1.

A printed circuit 8 has been disposed inside the body 2, which supports a sensitive sensor formed by a metal pellet 6, as well as the various electronic components intended, on the one hand, to manage the function of detection of the sensor and, on the other hand, to control the function consecutive to detection, namely the "freeze" of the image.

According to the invention, it is proposed to dispose between the sensor 6 and that part of the inner face of the body arranged plumb with the zone of detection 9, a foam element 14 of so-called electrostatic type, i.e. a conductive foam whose resistivity is less than 5 MΩ.cm. It has been observed that such an arrangement made it possible to avoid the aforementioned problems by "offsetting" to some extent the zone of sensitivity of the sensor 6 towards the inner wall of the camera located plumb with the zone of detection 9. It has been established that this foam had to be sufficiently conductive to propagate the capacitive effect of the sensor 6 and present a conductivity sufficiently low in order not to behave as if it constituted the sensor itself.

It is understood that the present invention is particularly interesting for the facilities that it offers concerning the design and production of this type of camera. In effect, on the one hand, it gives the designer freedom concerning the shape of the body of the camera insofar as the sensor may be remote from the zone of detection, and even off-centered with respect thereto and, on the other hand, it facilitates assembly.

Figure 4:
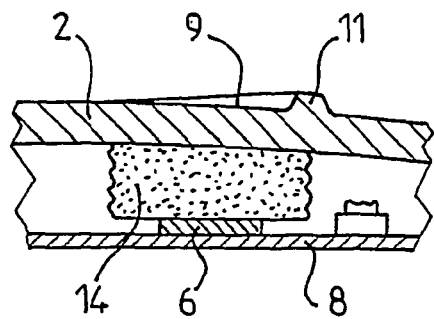
FIG. 4 is a partial view in vertical and longitudinal section of a variant embodiment of a camera according to the invention.

In a form of embodiment shown in FIG. 4, the ease of positioning the circuit 8 and the foam element 14 associated therewith is improved by giving the base of the latter dimensions greater than those of the sensor 6. In such an embodiment of the invention, in order to minimize the risks of short-circuits capable of being generated by the lower face of the foam when the latter comes into contact with the upper face of the circuit 8, a foam element 14 will be employed of which the resistivity of the lower face will be higher than that of its centre.

Thus, in a specific form of embodiment of the present invention shown in FIG. 4, a sensor 6 of circular shape and with a diameter of the order of 6 mm will be employed, as well as a foam element of cylindrical shape with a diameter equal to 8 mm and a height in the non-compressed state of 5 mm, this foam element having, after assembly, a thickness of 2.5 mm. It has been observed that, by choosing an electrostatic foam of which the resistivities of the upper and lower layers were respectively 300 kΩ.cm and 3000 kΩ.cm, the resistance between the layers being 1500 kΩ.cm, the precision and reliability of the detection were conserved with respect to an arrangement in which the sensor element 6 fast with its circuit 8 was applied against the inner face of the body of the camera.

Under these conditions, the camera according to the invention is used as set forth hereinafter. The user, when the camera 1 is positioned correctly, displaces one of his fingers, for example the thumb 12, over the body 2 of said camera until it encounters the stop 11. At that point, the user knows that any additional movement of his thumb in the same direction V will have the effect of being detected by the sensitive sensor 6 thus triggering off the desired operation. It will be understood that, insofar as the displacement of the user's finger is made over the surface of the body 2, brushing against the latter and not perpendicularly as would be the case of a switch of conventional type, this movement cannot provoke a sudden deviation of the camera 1.

The invention claimed is:

1. A camera for medical or dental, use, comprising:
an elongated casing (2) adapted to be held in a user's hand and provided at its anterior end with means for image-taking, the casing (2) comprising means for control (6, 8) of a sensitive type adapted to "freeze" on means for display (5) an image chosen by the user, the means for control comprising a zone of detection (9) located on the casing (2) which is defined by a surface discontinuity, a hollow or a crest (11),
wherein the casing (2) contains a sensor element (6) associated with an electronic piloting circuit (8) and an electrostatic foam element (14) of which one end is applied against the sensor element (6) and its opposite end is applied against a zone of an inner face of the casing (2) disposed plumb with the zone of detection (9), and
wherein the electrostatic foam element (14), when in position between the inner face of the casing (2) and the sensor element (6), is in a slightly compressed state.

2. The camera according to claim 1, wherein a part of the foam element (14) in contact with the sensor element (6) has a larger surface than that of the sensor element (6).

3. The camera according to claim 1, wherein a resistivity of the part of the foam element (14) in contact with the sensor element (6) is greater than the resistivity of a central part of the foam element (14).

4. The camera according to claim 1, wherein a resistivity of the part of the foam element (14) in contact with the inner face of the casing (2) is less than the resistivity of a central part of the foam element (14).

5. The camera according to claim 1, wherein a resistivity of the foam element (14) is less than 5 MΩ.cm.

6. The camera according to claim 1, wherein a thickness of the foam element (14) before compression is of an order of 5 mm and a resistivity of the foam element (14) in contact with the inner face of the casing (2) is of an order of 300 kΩ.cm, the resistivity of its opposite face is of an order of 3000 kΩ.cm and the resistivity of the central part of the foam element (14) between the extreme layers is of an order of 1500 kΩ.cm.

7. An assembly for medical or dental, use, comprising:
an elongated casing (2) adapted to be held in a user's hand and provided at its anterior end with a camera, the casing (2) comprising a controller (6, 8) of a sensitive type adapted to "freeze" on a display (5) an image chosen by the user, the controller further comprising a zone of detection (9) located on the casing (2) which is defined by a surface discontinuity, a hollow or a crest (11),
wherein the casing (2) contains a sensor element (6) associated with an electronic piloting circuit (8) and an electrostatic foam element (14) of which one end is applied against the sensor element (6) and its opposite end is applied against a zone of an inner face of the casing (2) disposed plumb with the zone of detection (9), and
wherein a part of the foam element (14) in contact with the sensor element (6) has a larger surface than that of the sensor element (6).

8. The assembly according to claim 7, wherein the electrostatic foam element (14), when in position between the inner face of the casing (2) and the sensor element (6), is in a slightly compressed state.

9. The assembly according to claim 7, wherein a resistivity of the part of the foam element (14) in contact with the sensor element (6) is greater than the resistivity of a central part of the foam element (14).

10. The assembly according to claim 7, wherein a resistivity of the part of the foam element (14) in contact with the inner face of the casing (2) is less than the resistivity of a central part of the foam element (14).

11. The assembly according to claim 7, wherein a resistivity of the foam element (14) is less than 5 MΩ.cm.

12. The assembly according to claim 7, wherein a thickness of the foam element (14) before compression is of an order of 5 mm and a resistivity of the foam element (14) in contact with the inner face of the casing (2) is of an order of 300 kΩ.cm, the resistivity of its opposite face is of an order of 3000 kΩ.cm and the resistivity of the central part of the foam element (14) between the extreme layers is of an order of 1500 kΩ.cm.

* * * * *